(12) United States Patent
Gordils Wallis

(10) Patent No.: US 7,163,396 B2
(45) Date of Patent: Jan. 16, 2007

(54) INSTRUMENT AND PROCESS FOR THE MINIMUM DISTANCE VERIFICATION BETWEEN TWO TEETH FOR THE PLACEMENT OF ONE OR TWO BONE INTEGRATED CYLINDRICAL OR SCREWED TYPE IMPLANTS IN DENSITY

(75) Inventor: Antonio Jose Gordils Wallis, Caracas (VE)

(73) Assignee: Innovative Implant Technology, LLC, Weston, FL (US)

( * ) Notice: Subject to any disclaimer, the term of this patent is extended or adjusted under 35 U.S.C. 154(b) by 0 days.

(21) Appl. No.: 11/068,515

(22) Filed: Feb. 28, 2005

(65) Prior Publication Data

US 2005/0191596 A1 Sep. 1, 2005

Related U.S. Application Data

(60) Provisional application No. 60/548,593, filed on Feb. 27, 2004.

(51) Int. Cl.
*A61C 19/04* (2006.01)

(52) U.S. Cl. .............................. 433/72; 433/76; 606/96

(58) Field of Classification Search .................. 606/96, 606/102; 433/72
See application file for complete search history.

(56) References Cited

U.S. PATENT DOCUMENTS 5,112,336 A * 5/1992 Krevolin et al. .............. 606/96
6,347,940 B1 * 2/2002 Gordils Wallis ............. 433/72

\* cited by examiner

*Primary Examiner*—Patricia Bianco
*Assistant Examiner*—Candice C. Stokes
(74) *Attorney, Agent, or Firm*—Gordon & Jacobson, PC

(57) ABSTRACT

An instrument for use in verifying that the distance between two teeth is the minimum adequate distance for the placement of one or two implants. The instrument verifies that marks made with a surgical splint have amongst them the minimum adequate distance, and centers edentulous space for placement of an implant or divides equidistantly the space for the placement of two implants. The instrument has a first rectangular sheet joined to one side of a second, larger rectangular sheet by an extension therebetween. A handle extends from the other side of the second rectangular sheet. The first and second rectangular sheets each have stops that extend from opposing sides of the respective sheets. The stops are adapted to engage teeth for proper positioning of the instrument during use.

2 Claims, 5 Drawing Sheets

I

II

III

IV

V

VI

I

IV

II

V

III

VI

INSTRUMENT AND PROCESS FOR THE MINIMUM DISTANCE VERIFICATION BETWEEN TWO TEETH FOR THE PLACEMENT OF ONE OR TWO BONE INTEGRATED CYLINDRICAL OR SCREWED TYPE IMPLANTS IN DENSITY

This application claims the benefit of U.S. Provisional Application No. 60/548,593 filed Feb. 27, 2004 and incorporates the same by reference.

FIELD OF INVENTION

This invention confirms that the edentuious space between teeth has the minimum distance necessary for the placement of one or two implants.

My prior invention disclosed in U.S. Pat. No. 6,347,940 of Feb. 19, 2002, confirms that the first and second marks were the implants are to be placed have the minimum distance amongst them and with the neighboring teeth.

This invention provides a better visual guide to determine the relation between the diameter of an implant and the alveolar rim and centralization of the distance between two teeth for the implant placement.

BACKGROUND

In many cases the distance between two teeth can be insufficient for one or two implants, which could generate an exaggerated proximity between the implant (s) and the neighboring teeth, obstructing the prosthetic restoration and creating hygiene problems which may compromise the case prognosis.

They are small titanium cylinders that behave as an artificial root, and they may provide:
  a method to anchor total upper and lower removable prosthetics;
  a method to place total or partial fixed prosthetics; and
  a method to replace a single tooth.

Step-by-step clinical procedures for this are:
  a) Pre-Medication;
  b) Anesthesia;
  c) Elevation of the total thickness flap;
  d) Placement of the surgical splint;
  e) Marking of the implant location;
  f) Use of Pilot Drill;
  g) Use of progressive diameter drills until reaching the diameter of the selected implant;
  h) Placement of the implant; and
  i) Second surgical phase for the placement of healing devices once the bone integration period as elapsed.

To these ends, the instrument of my prior U.S. patent has a first sheet which has a centered perforation joined by an extension to a second, larger sheet which has two perforations and, from the larger sheet, an extension joining it to handle for a process verifying space between teeth. However, the first and second sheets have only their shapes to determine their verification positions and, therefore, can be axially from one sheet to the other or angularly thereto out of their verification positions.

SUMMARY OF THE INVENTION

Therefore, an instrument which verifies whether the distance between two teeth is the minimum adequate distance for the placement of one or two implants, verifies that marks made with a surgical splint have amongst them the minimum adequate distance, and centers edentulous space for placement of an implant or divides equidistantly the space for the placement of two implants, the instrument having a first rectangular sheet with a central perforation joined by an extension from one side to one side of a second, larger rectangular sheet having two perforations and an opposite side from which one end of a handle extends is improved by stops extending from opposite ends of at least one of the one side of the first rectangular sheet or the opposite side of the second rectangular sheet for engaging the teeth in a position that verifies whether the distance between two teeth is the minimum adequate distance for the placement of one or two implants, verifies that marks made with a surgical splint have amongst them the minimum adequate distance, and centers edentulous space for placement of an implant or divides equidistantly the space for the placement of two implants.

In the preferred embodiments of this improvement to my prior U.S. Pat. No. 6,347,940, the stops are two extensions or prolongations added to each of the plates. The purpose our utility obtained at least with this preferred improvement is that, upon introducing the plates with one or two perforations between the teeth, the marks made to the bone are through plates stopped by the teeth. As described in the BACKGROUND above, the basic requirements in the placement of implants is that these be located in an adequate vestibular-lingual or vestibular-palatal position in order to achieve a correct distribution of forces for the prosthesis to be conformed without compromising aesthetic and maintenance conditions.

DESCRIPTION OF PREFERRED EMBODIMENTS

Figure 1:
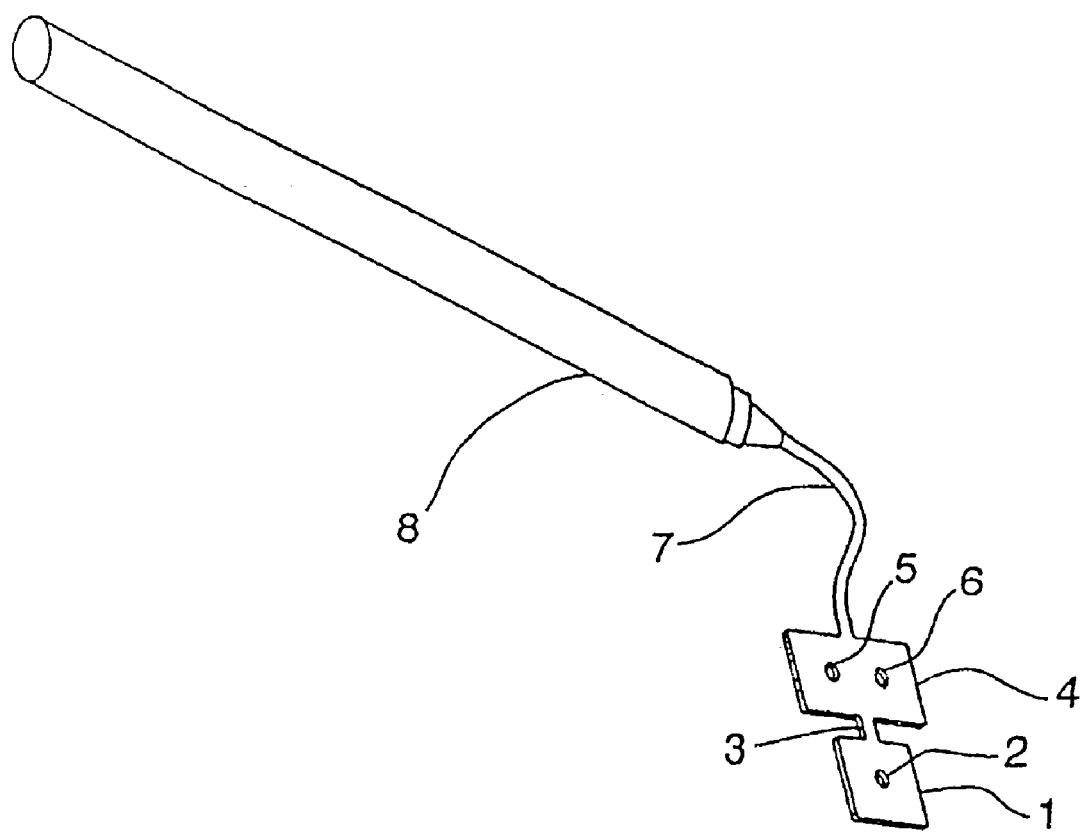
FIG. 1 is a perspective view of the instrument of my prior patent.
Figure 2:
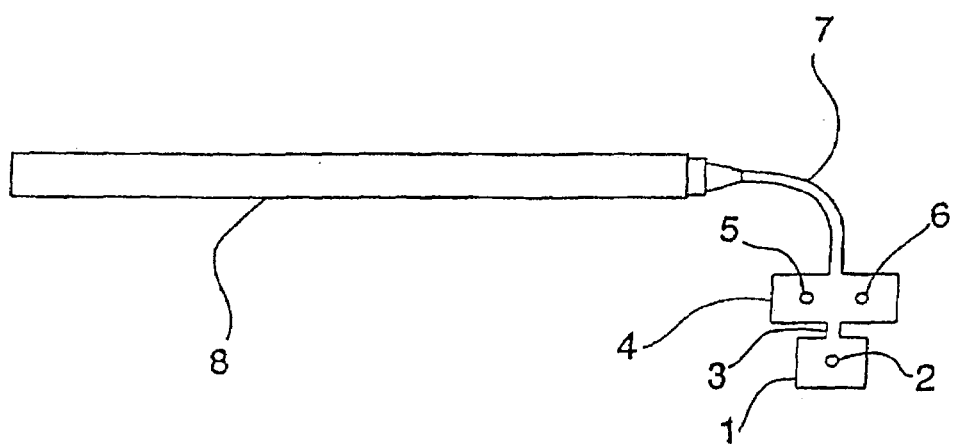
FIG. 2 is an elevational view of this instrument.

FIGS. 1 and 2 show the instrument of my prior patent U.S. Pat. No. 6,347,940. A first rectangular sheet 1 with a single perforation 2 is connected on one side by a member 3 to one side of a second, larger rectangular sheet 4 having two perforations 5, 6. A member 7 connects an opposite side of the second sheet 4 to one end of a handle 8.

Figure 3:
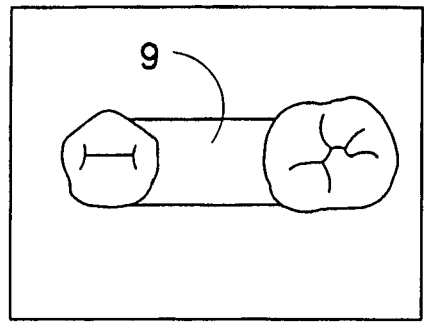
FIG. 3 is a schematic sequence showing the procedure steps in which this instrument is used.
Figure 3:
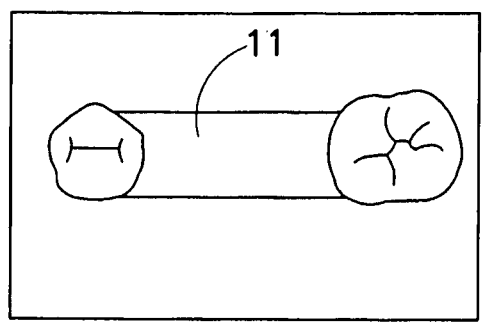
Figure 3:
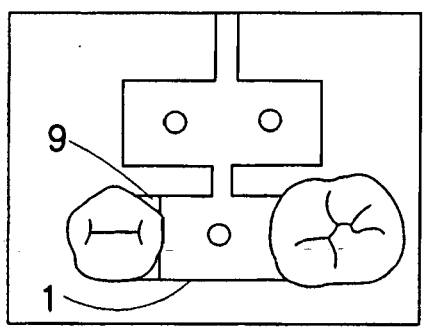
Figure 3:
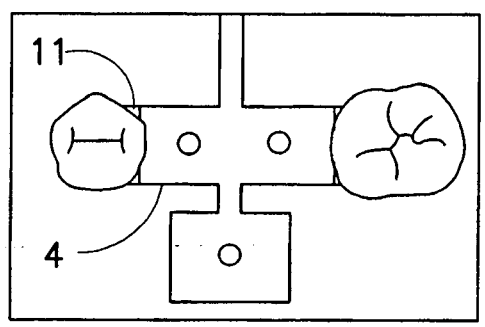
Figure 3:
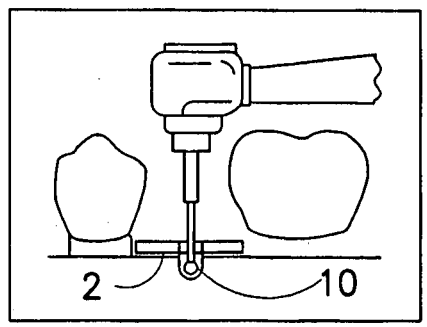
Figure 3:
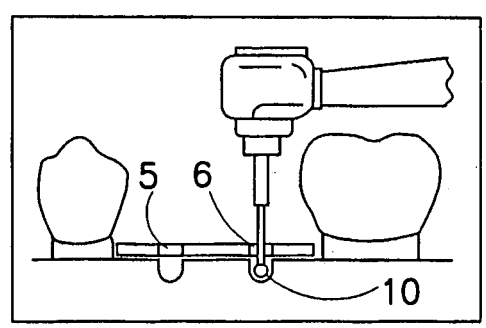

FIG. 3 shows the use of the prior instrument. Specifically, FIG. 3(I) shows the edentulous space 9 between two teeth where the implant will be placed. FIG. 3(II) shows the first sheet 1 with a perforation 2 (FIG. 3(III) located in the edentulous space 9 between two teeth and the minimum adequate distance is verified for the placement of the implants. FIG. 3(III) with a round drill 10 through the perforation 2 the bone is marked achieving and equidistant distribution of the edentulous space. FIG. 3(IV) edentulous space 11 between two teeth where the implants will be placed. In FIG. 3(V) the second sheet 4 with two perforations is placed in the edentulous space 11 between the teeth and the minimum adequate distance is verified for the placement of the two implants. FIG. 3(VI) with a round drill 10 through the perforations 5 and 6 the bone is marked achieving and equidistant distribution of the endentulous space.

Figure 4:
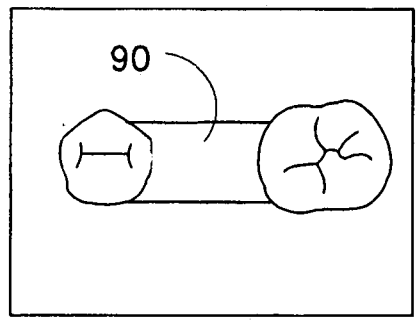
FIG. 4 is a schematic sequence showing the procedure steps in which the instrument of the present invention is used.
Figure 4:
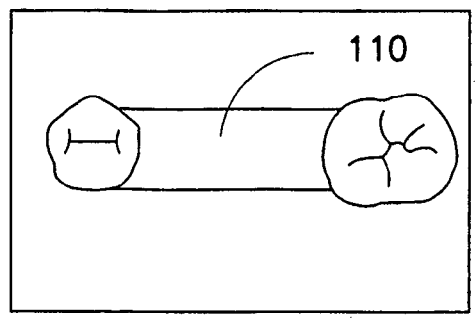
Figure 4:
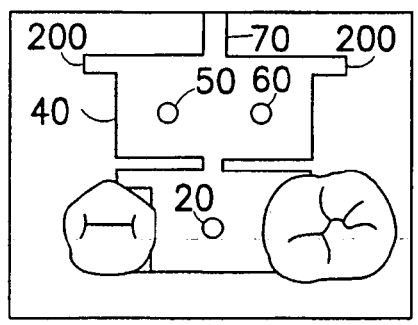
Figure 4:
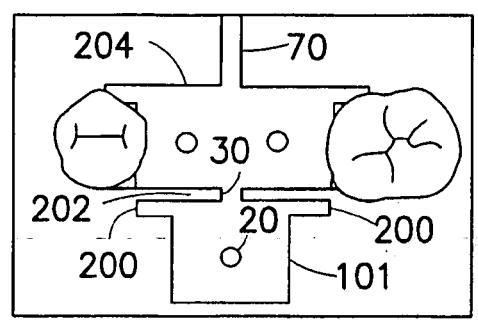
Figure 4:
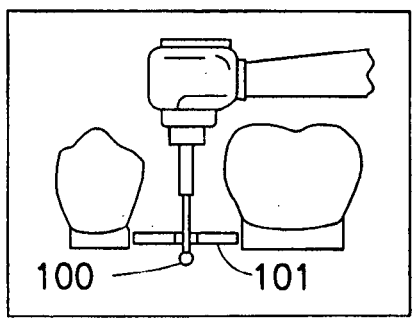
Figure 4:
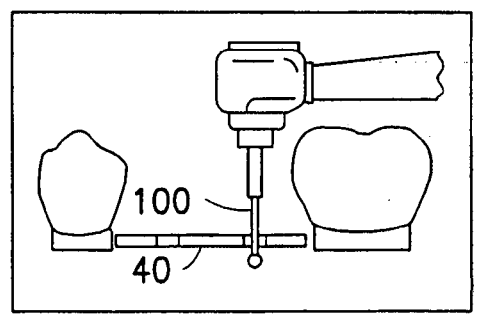
Figure 5:
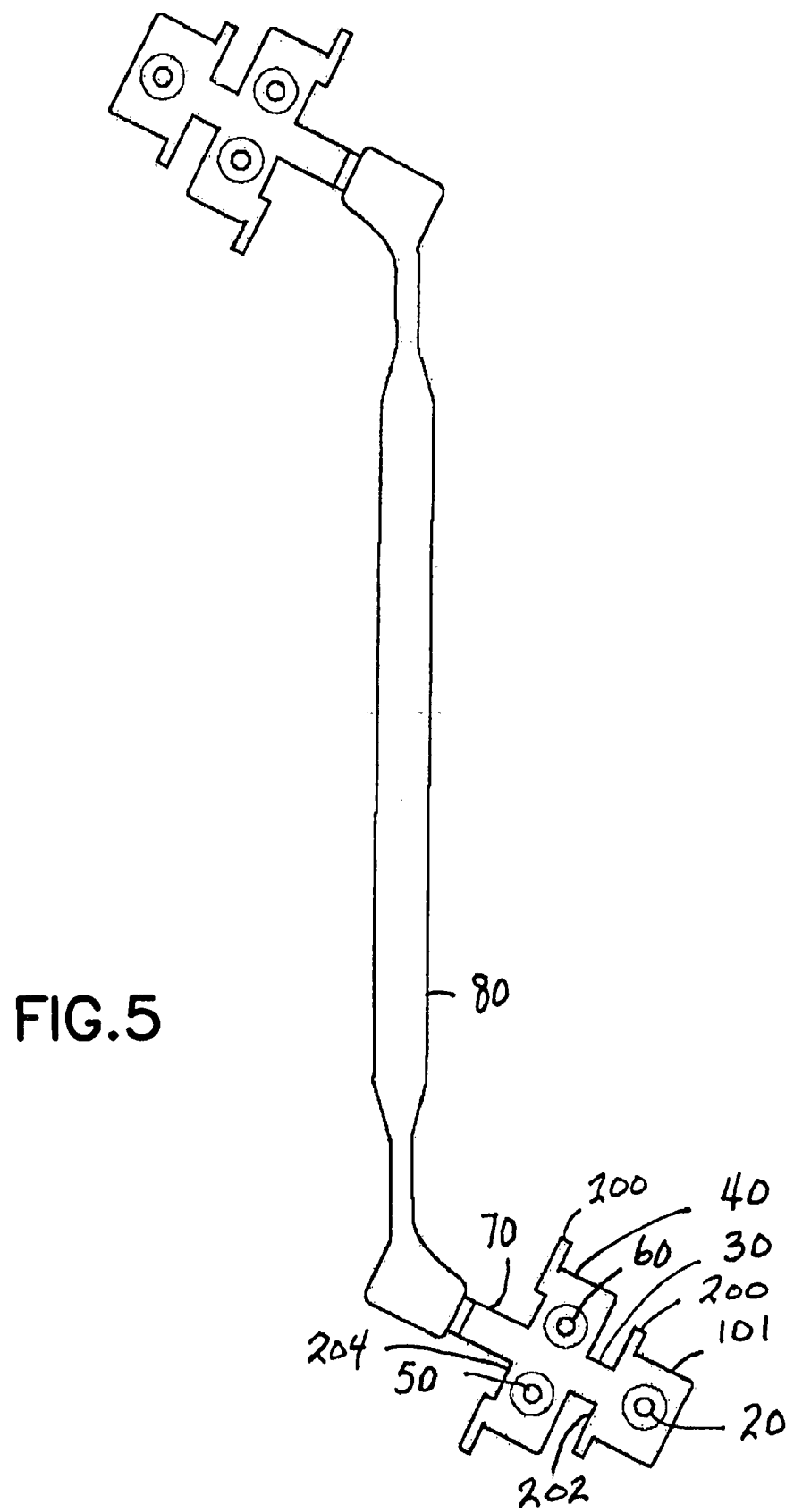
FIG. 5 is a plan view of the instrument of FIG. 4.

FIGS. 4 and 5 show the instrument of the present invention in at least general correspondence with FIGS. 3 and 1, respectively. Portions of this instrument that correspond to the instrument of my prior patent have corresponding reference characters with the addition of a zero (except first sheets 1 and 101) and, therefore, need not be further described.

FIGS. 4 and 5 show that the present invention improves the instrument with by stops 200 extending from opposite ends of at least one of the one side 202 of the first rectangular sheet or the opposite side 204 of the second rectangular sheet for engaging the teeth in a position that verifies the distance between the teeth. The stops 200 engage the teeth on the opposite sides of the edentuious space between the teeth when the first and second sheets are positioned for verifying whether the distance between two teeth is the minimum adequate distance for the placement of one or two implants, verifies that marks made with a surgical splint have amongst them the minimum adequate distance, and centers edentulous space for placement of an implant or divides equidistantly the space for the placement of two implants.

As shown in FIG. 5., sheets corresponding to the first and second sheets 101 and 40 are on the opposite end of the handle 80.

Variations, combinations and permutations of the invention as may occur to those of ordinary skill in the art are contemplated as within the scope of the following claims.

What is claimed is:

1. In an instrument which verifies whether the distance between two teeth is the minimum adequate distance for the placement of one or two implants, verifies that marks made with a surgical splint have amongst them the minimum adequate distance, and centers edentulous space for placement of an implant or divides equidistantly the space for the placement of two implants, the instrument having a first rectangular sheet with a central perforation joined by an extension from one side to one side of a second, larger rectangular sheet having two perforations and an opposite side from which one end of a handle extends, the improvements comprising:

stops extending from opposite ends of at least one of the one side of the first rectangular sheet or the opposite side of the second rectangular sheet for engaging the teeth in a position that verifies whether the distance between two teeth is the minimum adequate distance for the placement of one or two implants, verifies that marks made with a surgical splint have amongst them the minimum adequate distance, and centers edentulous space for placement of an implant or divides equidistantly the space for the placement of two implants.

2. The instrument according to claim 1, and further comprising at least one of a sheet corresponding to the first or second sheets on an opposite end of the handle.

* * * * *

UNITED STATES PATENT AND TRADEMARK OFFICE
CERTIFICATE OF CORRECTION

| | | |
|---|---|---|
| PATENT NO. | : 7,163,396 B2 | Page 1 of 1 |
| APPLICATION NO. | : 11/068515 | |
| DATED | : January 16, 2007 | |
| INVENTOR(S) | : Antonio Jose Gordils Wallis | |

It is certified that error appears in the above-identified patent and that said Letters Patent is hereby corrected as shown below:

Cover Page (54) and at column 1, line 6 in the title "DENSITY" should be replaced with --DENTISTRY--

Signed and Sealed this

Twentieth Day of March, 2007

JON W. DUDAS
*Director of the United States Patent and Trademark Office*